United States Patent [19]

Ternström

[11] Patent Number: 4,627,846
[45] Date of Patent: Dec. 9, 1986

[54] INCONTINENCE SHIELD FOR MEN
[75] Inventor: Maj I. Ternström, Mölnlycke, Sweden
[73] Assignee: Molnlycke AB, Goteborg, Sweden
[21] Appl. No.: 620,081
[22] Filed: Jun. 12, 1984
[30] Foreign Application Priority Data
  Jun. 27, 1983 [SE] Sweden .................. 8303663
[51] Int. Cl.[4] .............................................. A61F 5/44
[52] U.S. Cl. ............................ 604/349; 604/385 R; 128/162
[58] Field of Search ................ 604/385 R, 386, 387, 604/392, 393, 398, 400, 358, 346–349, 304, 308, 317, 327, 355, 350–353; 128/158–162

[56] References Cited
U.S. PATENT DOCUMENTS

| | | | |
|---|---|---|---|
| 1,228,452 | 6/1917 | Lawrence | 604/353 |
| 3,621,846 | 11/1979 | Lehman | 128/159 |
| 4,197,849 | 4/1980 | Bostick | 4/144.3 |
| 4,437,860 | 3/1984 | Sigl et al. | 604/385 A |
| 4,453,938 | 6/1984 | Brendling | 604/346 |
| 4,500,314 | 2/1985 | Brendling | 604/346 |

FOREIGN PATENT DOCUMENTS

| | | | |
|---|---|---|---|
| 0069946 | 9/1892 | Fed. Rep. of Germany | 128/161 |
| 325102 | 6/1970 | Sweden . | |
| 426206 | 12/1982 | Sweden . | |

Primary Examiner—Dalton L. Truluck
Assistant Examiner—Karen L. Kaechele
Attorney, Agent, or Firm—Young & Thompson

[57] ABSTRACT

The present invention relates to an incontinence shield for men, intended to embrace the penis.

The invention is characterized in that the shield has a front-piece and a back-piece and a center-piece which is narrower in relation thereto;
  that the shield is arranged to embrace both the penis and the scrotum of the wearer;
  that to this end the back-piece has therein a recess extending from the end edge thereof;
  and in that wing-like portions formed on the back-piece by the recess on both sides thereof are arranged to be firmly clamped beneath the scrotum of the wearer, to hold the shield firmly in position.

10 Claims, 3 Drawing Figures

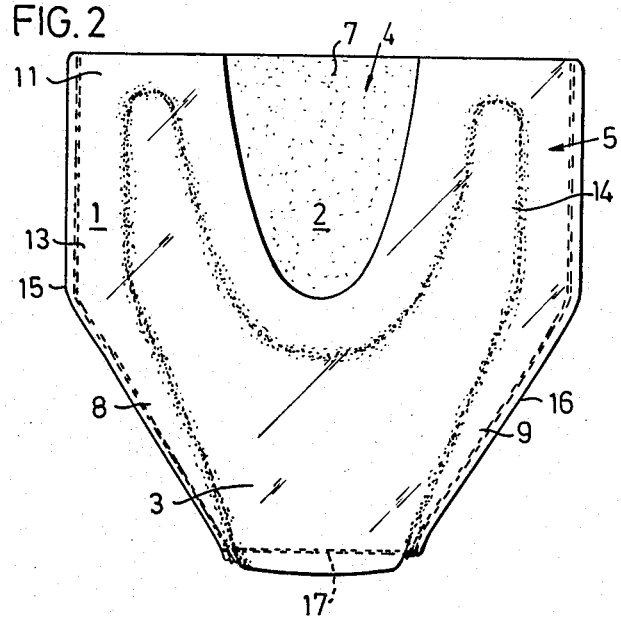
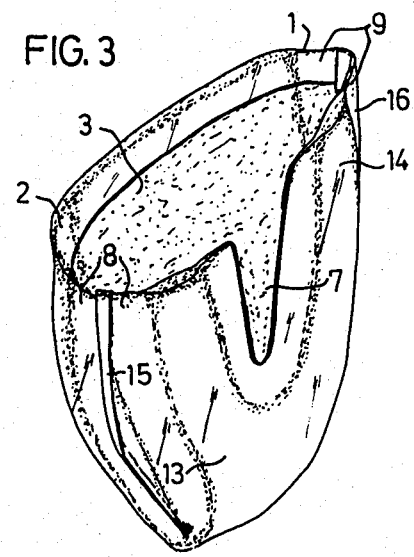

INCONTINENCE SHIELD FOR MEN

FIELD OF THE INVENTION

The present invention relates to an incontinence shield for men, of the kind which is intended to surround the penis of the wearer fully or partially, in a container-like manner, and which comprises an outer side comprising a liquid-impermeable material, an inner side of liquid-permeable material, and an intermediate body of absorbent material.

BACKGROUND OF THE INVENTION

Hitherto known incontinence shields normally comprise conventional diapers, which are substantially planar and, for example, of rectangular shape. Such diapers, however, are intended for the absorption of urine and excretement, and are thus unsuitable for persons who solely require a urine-collecting incontinence shield or guard. The diaper must have a certain width and the absorbent body must have a given thickness, in order to have satisfactory absorption ability. Naturally, the diaper takes up an equivalent amount of room between the legs of the wearer, causing discomfort to the wearer, in the form of chafing, sores etc. In the case of diapers, there is also a serious risk that excreted body fluids will leak past the edges of the diaper, when the diaper becomes saturated and is compressed between the legs of the wearer during wear.

It is known to give the incontinence shield a container-like form, in which the shield comprises an outer layer of liquid-impermeable material and an absorbent material arranged therein. Shields of this kind function quite satisfactorily in the case of men with a penis of normal size, which can be accomodated in the container and embraced thereby. Under certain conditions, however, and particularly when the penis of the wearer is relatively small, there is a serious risk of the penis leaving its position in the container.

One particular problem is that of providing a suitable incontinence shield for older men whose penises are retarded and so small that they cannot be accomodated satisfactorily in a hose-like casing.

The SE Patent Specification No. 426 206 describes an incontinence shield in which, in an attempt to solve the problem of holding the container-like shield in position also with men whose penis is small or retarded, said shield is arranged to be brought into sealing abutment with the body of the wearer in the area around the root or base of the penis, thereby to try to hold the container more securely.

The shield according to this publication has the form of a flat hose-like member having two pairs of mutually opposing edges. The hose-like member has the form of a parallelogram, of which three edges are closed and the fourth edge has been left open. Thus, there is obtained at the opening an acute corner and an obtuse corner. When the shield is worn, the acute corner is turned to face upwards and the obtuse corner is turned to face downwards. As opposed to other known urine-collecting containers in which the opening edge lies at right angles to the long axis of the container, in the shield according to the aforesaid publication the side edges of said opening extend obliquely upwards, along the sides of the root of the penis, it being maintained that in this way the penis is held relatively securely in position, even when the penis of the wearer is relatively small.

The aforedescribed incontinence shields, which are solely intended to embrace the penis of the wearer, do not function entirely satisfactorily and are readily able to slip from their intended position.

The present invention is based on the concept of using the scrotum or testicle-pouch of the wearer, in addition to his penis, as a means for holding an incontinence shield safely around said penis.

Accordingly, this invention is characterized in that the shield has a front-piece, a back-piece and a centre-piece (or a connecting line) which connects said front-piece and said back-piece and which is narrower in relation thereto and which serves as the bottom of the container-like shield; in that the shield is arranged to embrace both the penis and the testicle-pouch of the wearer; in that to this end the back-piece is provided with a slit or recess which extends from the end edge of said back-piece; and in that wing-like portions formed on the back-piece by said slit or said recess and located on both sides thereof are intended to be clamped firmly against the body of the wearer, beneath the testicle-pouch thereof. The absorbent body of the shield is suitably soft and compressible, and in addition to functioning as an absorption medium is also intended to impart a given requisite stability to the wing-like portions, to enable said wing-like portions to be compressed and moulded beneath the testicle-pouch of the wearer, so as to hold the shield firmly.

Because the shield is intended to embrace both the penis and testicle-pouch of the wearer, the shield will be held more positively, even when the penis of the wearer is small.

According to one suitable embodiment, the inner and outer sides of the shield have portions which extend laterally beyond the absorbent body and there joined together.

In order to form a closed, liquid-tight container, the outer edges of said portions on the front-piece of the shield are sealingly joined to corresponding portions on the back-piece thereof.

The lateral extension of the absorbent body in the centre-piece should not be too great, since the crutch of the wearer might otherwise become chafed. When seen longitudinally, the size of the front-piece and back-piece of the shield is chosen so as to accomodate both the penis and the testicle-pouch of the wearer. In order to avoid chafing of the crutch of the wearer, the lateral extension of the absorbent body shall be less than one-half the length of the front-piece and back-piece respectively, and suitably greater than one-quarter of said length, in order to provide a satsifactory absorption capacity.

In order that the centre-piece of the shield is able to accomodate the testicle-pouch of the wearer, the inner and outer sides of the shield shall have a lateral extension which is substantially from 1.5 to 2.0 times the extension of the absorbent layer.

In accordance with one suitable embodiment, a pre-tensioned elastic thread or the like is arranged across the centre-piece, in a manner to gather the sharp edges extending beyond the absorbent layer and formed by the outer and inner sides of the shield.

The recess formed in the back-piece of the shield is substantially of U-shape, thereby to obtain close, sealing abutment with the body of the wearer, around the base of the testicle-pouch.

Additionally hereto, in accordance with another suitable embodiment of the invention, one or more pre-tensioned elastic threads or the like may be arranged transversely of the shield, so as to tighten the shield around the penis and testicle-pouch of the wearer.

BRIEF DESCRIPTION OF THE DRAWINGS

The invention will now be described in more detail with reference to embodiments thereof illustrated in the accompanying drawings, in which FIG. 2 is a plan view of a shield similar to that illustrated in FIG. 1, but seam-welded to form a closed container; and FIG. 3 is a perspective view of the shield illustrated in FIG. 2.

DETAILED DESCRIPTION OF THE INVENTION

Figure 1:
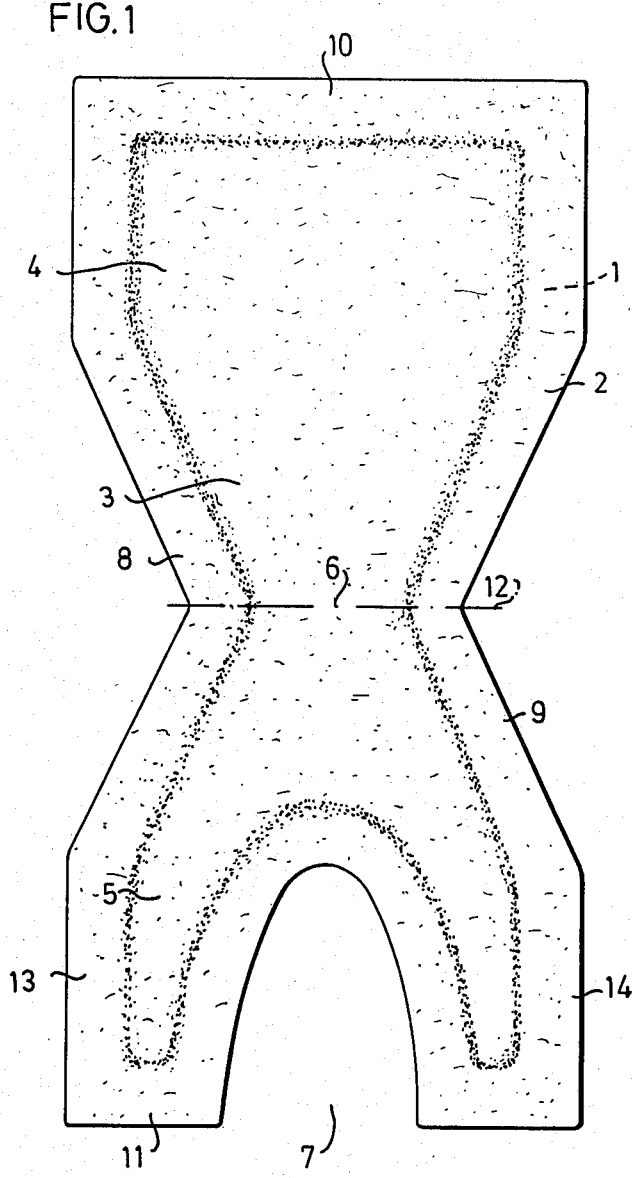
FIG. 1 illustrates a shield according to a first embodiment in a flattened state.

The shield according to the invention comprises an outerside 1 made of liquid-impermeable material, such as polyethylene, an inner-side 2 made of a liquid-permeable material, preferably non-woven material, and an intermediate absorbent layer or body 3, suitably comprising fluff pult. The shield has a front-piece 4, a back-piece 5 and a centre-piece 6 which is narrow in relation to said front and back pieces.

Arranged in the back-piece 5 is a recess 7, said back-piece being located behind the testicle-pouch of the wearer when the shield is worn. The recess 7 is substantially of U-shape configuration, as shown in FIG. 1.

The inner and outer sides of the shield, i.e. the liquid-permeable and liquid-impermeable layers, have portions 8, 9, 10 and 11 which extend beyond and around the absorbent layer and which are mutually joined together.

When the shield is to be placed on the wearer, it is folded around the centre line 12 and the front-piece 4 is brought in front of the penis and testicle-pouch, while the back-piece 5 is placed therebehind.

The U-shaped recess 7 is brought around the testicle-pouch, so that the defining edges of said recess lie tightly against the base of said pouch. When the shield is brought into position, the wing-like portions situated on both sides of the recess, said wing-like portions being referenced 13 and 14 respectively, will be located beneath the testicle-pouch of the wearer. Those portions of the absorbent layer or body adjacent said wing-like portions, and also the remainder of the absorbent body have a thickness in the order of at least 5 mm, and are soft and compressible. Because the wing-like portions have a given thickness and are compressible, they are clamped positively and firmly against the body, beneath the testicle-pouch of the wearer, and contribute greatly to holding the applied shield firmly in position. The shield illustrated in FIG. 1 is held in position with the aid of suitable elastic pants, with which the edge parts on the front-piece of the shield are pressed into abutment with the edge parts of the back-piece thereof. The shield will therefore embrace the penis and testicle-pouch of the wearer in a container-like fashion.

The shield illustrated in FIGS. 2 and 3 differs from that described above, insofar that subsequent to having been folded along the centre line, the front and back-pieces 4 and 5 have been joined together along the edges 15 and 16 of the layers projecting beyond the absorbent body, i.e. the edges of the inner and outer sides of the shield. Those elements of the shield illustrated in FIGS. 2 and 3 which correspond to similar elements in FIG. 1 have been given the same reference numerals. In order to avoid the formation of sharply pointed projecting corners at the centre-piece of the outer and inner sides of the shield, such corners being liable to chafe the inside of the thighs of the wearer, the shield is provided at said centre-piece with a pre-tensioned elastic thread 17. This thread is intended to gather the sharp edges at the bottom of the shield, so as to eliminate said edges.

As a result of joining together the front and back pieces of the shield along the edges 15,16, for example with the aid of seam welds, there is obtained a closed container with which, compared with the embodiment illustrated in FIG. 1, risk of leakage around the sides of the shield has been completely eliminated.

In order to avoid chafing of the crutch of the wearer, the lateral extension of the absorbent body at said centre-piece, i.e. the bottom of the container, should not greatly exceed 50 mm. This lateral extension at the container bottom, however, is not large enough to accomodate the penis and testicle-pouch of the wearer. Consequently, the layers 1 and 2 forming the inner and outer sides of the shield extend substantially beyond the absorbent body or layer 3 at said centre-piece, and should there have a total width in the order of 90 mm, in order to accomodate pouch and penis. In order to accomodate the pouch and penis comfortably, the distance between the bottom of the formed contained and the apex of the U-shaped recess 7 should slightly exceed half the length of the back-piece 5 and is normally in the order of 85 mm. Normally, the front-piece and the back-piece are of the same length, normal size about 150 mm. In this case the depth of the recess 7 is suitably 60-70 mm.

Thus, the shield described with reference to FIGS. 2 and 3 is drawn tightly around both penis and testicle-pouch, thereby holding the shield firmly in place, even though the penis of the wearer is small. As described before, when compared with previously known incontinence shields intended solely to embrace the penis of the wearer, further improvement in holding the shield firmly in place is obtained with the shield according to the invention through the agency of the wing-like portions 13 and 14, which are firmly clamped beneath the testicle-pouch of the wearer. Tightening of the shield around penis and testicle-pouch can be amplified by the inclusion of pre-stretched elastic threads or the like (not shown) either partially or completely around the shield.

The invention is not limited to the aforedescribed embodiment, since several modifications are possible within the scope of the following claims.

For example, the recess in the back-piece 5 of the shield need not be U-shaped, but may comprise a narrow slit which widens and conforms to the body of the wearer as the shield is put on.

In the FIG. 1 embodiment, the centre-piece principally comprises the connecting line 6 located between the front-piece 4 and the back-piece 5, and the portions of said front and back-pieces lying adjacent said line. Alternatively hereto, a separate, defined centre-piece may be located between the front and back pieces of the shield. In each case, the shield may be produced in the form of a single-piece article or the front-piece, back-piece and optionally also the intermediate piece may be made separately and then joined together.

As an alternative to the shield described with reference to FIG. 1, a shield produced in the form of a flat blank may be coated with an adhesive along its edges so that when placing the shield in position, the wearer himself can join respective edges together, to produce the container-like shape.

Suitably, the side-edge joins are so made as to be readily broken manually, both when the joins are made with the aid of an adhesive and when said side-edges are seam welded in accordance with the embodiments of FIGS. 2 and 3. This enables the wearer to open the shield after use, so that it can be taken off more readily.

I claim:

1. An incontinence shield for men intended to embrace the penis of the wearer either fully or partially in a container-like fashion, and comprising an outer-side made of liquid-impermeable material, an innerside made of liquid-permeable material, and an intermediate body of absorbent material, the shield further comprising a front-piece, a back-piece and a centre-piece which connects said front-piece and said back-piece and is narrower than said pieces and forms the bottom of said container; the shield being arranged to embrace both the penis and the scrotum of the wearer;

the back-piece having a slit or recess which extends from the free edge thereof; wing-like portions formed by said slit or recess and located on respective sides thereof adapted to be clamped securely against the body of the wearer, beneath the scrotum thereof, the absorbent body being soft and compressible, and in addition to functioning as an absorption medium being also arranged to impart a given requisite stability to said wing-like portions, so as to be compressibly mouldable beneath the scrotum of the wearer, thereby to hold the shield firmly in position.

2. A shield according to claim 1, characterized in that the front and back-pieces have the form of a single-piece structure having a centre-piece; and in that said structure is folded double or arranged to be folded about said centre-piece, to form said container-like shield.

3. A shield according to claim 1, characterized in that the inner and outer sides of said shield have portions which extend laterally beyond the absorbent body and are there joined together.

4. A shield according to claim 3, characterized in that the outer edges of said portions on the front-piece are sealingly joined to corresponding portions on the back-piece in a manner to form a closed water-tight container.

5. A shield according to claim 1, characterized in that in order to avoid chafing in the crotch of the wearer, the lateral extension of the absorbent body at the centre-piece is smaller than one-half the length of the front-piece and the back-piece and suitably greater than one-quarter of said length.

6. A shield according to claim 5, characterized in that the inner and outer sides of the shield at the centre-part thereof have a lateral extension which is substantially from 1.5 to 2.0 times the extension of the absorbent body, so as to provide accomodation for the scrotum of the wearer.

7. A shield according to claim 6, characterized in that a pre-tensioned elastic thread or the like is arranged across the centre-piece, so as to draw-in the sharp edges formed by the outer and inner sides of the shield and extending beyond the absorbent body.

8. A shield according to claim 1, characterized in that the depth of the slit or recess measured from said end edges is from $\frac{1}{4}$ to $\frac{3}{4}$ of the length of the back-piece.

9. A shield according to claim 1, characterized in that the recess in the back-piece of the shield is substantially of U-shape.

10. A shield according to claim 1, characterized in that one or more pre-tensioned elastic threads are arranged transversally to the shield, to draw the shield firmly around the penis and scrotum of the wearer.

* * * * *